(12) United States Patent
Miller et al.

(10) Patent No.: US 8,124,797 B2
(45) Date of Patent: Feb. 28, 2012

(54) EPOXIDATION PROCESS

(75) Inventors: Jay F. Miller, Chester Springs, PA (US); John H. Speidel, Jr., Media, PA (US)

(73) Assignee: Lyondell Chemical Technology, LP, Houston, TX (US)

( * ) Notice: Subject to any disclaimer, the term of this patent is extended or adjusted under 35 U.S.C. 154(b) by 433 days.

(21) Appl. No.: 12/459,065

(22) Filed: Jun. 26, 2009

(65) Prior Publication Data

US 2010/0331556 A1 Dec. 30, 2010

(51) Int. Cl.
*C07D 301/12* (2006.01)
*C07D 301/06* (2006.01)

(52) U.S. Cl. ........................ 549/531; 549/533

(58) Field of Classification Search .............. 549/531, 549/533
See application file for complete search history.

(56) References Cited

U.S. PATENT DOCUMENTS

| | | | |
|---|---|---|---|
| 3,351,635 A | 11/1967 | Kollar | |
| 4,367,342 A | 1/1983 | Wulff et al. | |
| 4,410,501 A | 10/1983 | Taramasso et al. | |
| 4,666,692 A | 5/1987 | Taramasso et al. | |
| 4,833,260 A | 5/1989 | Neri et al. | |
| 4,859,785 A | 8/1989 | Bellussi et al. | |
| 4,937,216 A | 6/1990 | Clerici et al. | |
| 5,859,265 A | 1/1999 | Müller et al. | |
| 6,498,259 B1 | 12/2002 | Grey et al. | |
| 6,555,493 B2 | 4/2003 | Cooker et al. | |
| 6,759,540 B2 | 7/2004 | Oguchi et al. | |
| 7,030,255 B2 | 4/2006 | Grey et al. | |

FOREIGN PATENT DOCUMENTS

| JP | 4-352771 | 5/1991 |
|---|---|---|
| WO | WO 98/00413 | 1/1998 |

OTHER PUBLICATIONS

Wu et al., "A Novel Titanosilicate with MWW Structure. I. Hydrothermal Synthesis, Elimination of Extraframework Titanium, and Characterizations," Journal of Physical Chemistry B, 105, (2001), p. 2897-2905.

*Primary Examiner* — Bernard Dentz

(57) ABSTRACT

This invention is a process for producing propylene oxide. The process comprises first contacting a titanium zeolite with a reaction feed comprising propylene, hydrogen peroxide, tertiary butyl alcohol, and water to produce a product stream comprising propylene, propylene oxide, propylene glycol, tertiary butyl alcohol, and water. The product stream is distilled to produce a first overhead stream comprising propylene and a first bottoms stream comprising propylene oxide, propylene glycol, tertiary butyl alcohol, and water. The first bottoms stream is distilled to produce a second overhead stream comprising propylene oxide and a second bottoms product stream comprising propylene glycol, tertiary butyl alcohol, and water. The second bottoms stream is distilled to produce a third overhead stream comprising an azeotrope of tertiary butyl alcohol and water and a third bottoms stream comprising propylene glycol and water.

13 Claims, 1 Drawing Sheet

EPOXIDATION PROCESS

FIELD OF THE INVENTION

This invention relates to a process for producing propylene oxide.

BACKGROUND OF THE INVENTION

Propylene oxide is an important industrial chemical. Propylene oxide is commercially produced by reacting propylene with an organic hydroperoxide oxidizing agent, such as ethylbenzene hydroperoxide or tert-butyl hydroperoxide. This process is performed in the presence of a solubilized molybdenum catalyst, see U.S. Pat. No. 3,351,635, or a heterogeneous titania on silica catalyst, see U.S. Pat. No. 4,367,342.

Propylene oxide can also be produced by the epoxidation of propylene using hydrogen peroxide. U.S. Pat. Nos. 4,833,260, 4,859,785, and 4,937,216, for example, disclose olefin epoxidation with hydrogen peroxide in the presence of a titanium silicate catalyst.

Much current research is conducted in the direct epoxidation of propylene with oxygen and hydrogen. In this process, it is believed that oxygen and hydrogen react in situ to form an oxidizing agent. Many different catalysts have been proposed for use in the direct epoxidation process. Typically, the catalyst comprises a noble metal and a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 6,498,259 describes a catalyst mixture of a titanium zeolite and a supported noble metal complex. The noble metal is supported on a carrier such as carbon, titania, zirconia, niobium oxides, silica, alumina, silica-alumina, tantalum oxides, molybdenum oxides, tungsten oxides, titania-silica, zirconia-silica, niobia-silica, and mixtures thereof. Other direct epoxidation catalyst examples include gold supported on titanosilicates, see for example PCT Intl. Appl. WO 98/00413.

The direct epoxidation process may occur in the liquid or vapor phase. When the process is performed in the liquid phase, the liquid medium is usually an alcohol-water mixture, most typically methanol and water.

In sum, new methods to produce propylene oxide by epoxidation of propylene are needed.

SUMMARY OF THE INVENTION

This invention is a process for producing propylene oxide. The process comprises first contacting a titanium zeolite with a reaction feed comprising propylene, hydrogen peroxide, tertiary butyl alcohol, and water to produce a product stream comprising propylene, propylene oxide, propylene glycol, tertiary butyl alcohol, and water. The product stream is distilled to produce a first overhead stream comprising propylene and a first bottoms stream comprising propylene oxide, propylene glycol, tertiary butyl alcohol, and water. The first bottoms stream is distilled to produce a second overhead stream comprising propylene oxide and a second bottoms product stream comprising propylene glycol, tertiary butyl alcohol, and water. The second bottoms stream is distilled to produce a third overhead stream comprising an azeotrope of tertiary butyl alcohol and water and a third bottoms stream comprising propylene glycol and water.

DETAILED DESCRIPTION OF THE INVENTION

Figure 1:
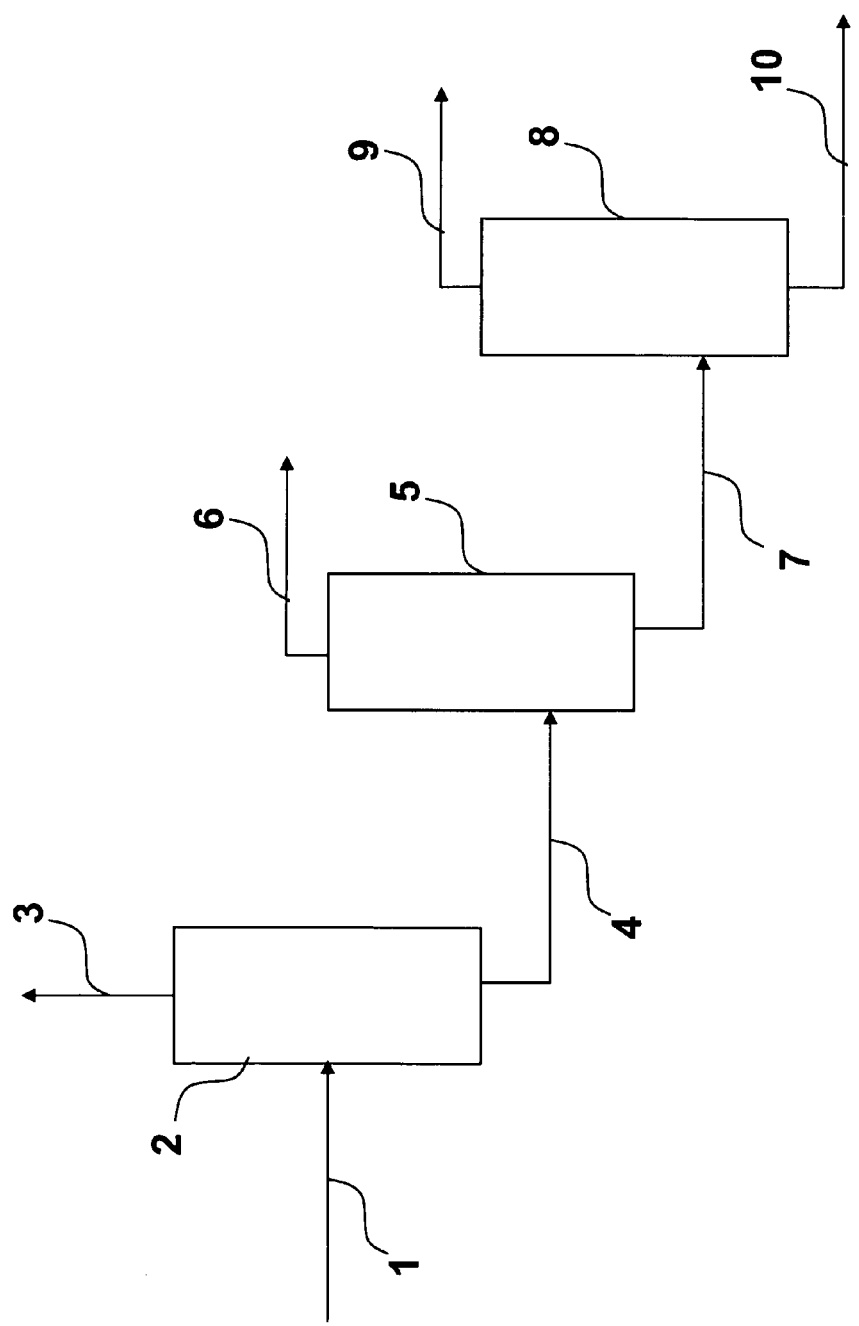
FIG. 1 is a schematic flow diagram of one embodiment of the invention.

The process of the invention comprises epoxidizing propylene to produce propylene oxide. The epoxidation step of the process comprises contacting a titanium zeolite with a reaction feed comprising propylene, hydrogen peroxide, tertiary butyl alcohol, and water to produce a product stream comprising propylene, propylene oxide, propylene glycol, tertiary butyl alcohol, and water.

Titanium zeolites are well known. Titanium zeolites comprise the class of zeolitic substances wherein titanium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium zeolites are those crystalline materials having a porous molecular sieve structure with titanium atoms substituted in the framework. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), "TS-3" (as described in Belgian Pat. No. 1,001,038), and titanium-MWW (having a topology analogous to that of the MWW aluminosilicate zeolites). Titanium-containing molecular sieves having framework structures isomorphous to zeolite beta, mordenite, ZSM-48, ZSM-12, ZSM-22, SBA-15, TUD, HMS, and MCM-41 are also suitable for use. Titanium-MWW (Ti-MWW) is particularly preferred. Ti-MWW, and its production, is well known in the art. See for example, U.S. Pat. No. 6,759,540 and Wu et al., J. Phys. Chem. B, 2001, 105, p. 2897.

The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2 (1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The epoxidation step of the process comprises contacting propylene, hydrogen peroxide, tertiary butyl alcohol (TBA), and water in the presence of the titanium zeolite catalyst. The hydrogen peroxide may be generated prior to use in the epoxidation reaction. Pre-formed hydrogen peroxide may be derived from any suitable source, including oxidation of secondary alcohols such as isopropanol, the anthraquinone process, and from direct reaction of hydrogen and oxygen. The concentration of the hydrogen peroxide reactant added into the epoxidation reaction is not critical. Typical hydrogen peroxide concentrations range from 0.1 to 90 weight percent hydrogen peroxide in the TBA-water mixture, preferably 2 to 10 weight percent.

The amount of hydrogen peroxide to the amount of propylene is not critical, but most suitably the molar ratio of hydrogen peroxide: propylene is from 100:1 to 1:100, and more preferably in the range of 10:1 to 1:10. One equivalent of hydrogen peroxide is theoretically required to oxidize one equivalent of propylene, but it may be desirable to employ an excess of one reactant to optimize selectivity to propylene oxide.

The hydrogen peroxide may also be generated in situ by the reaction of hydrogen and oxygen in the presence of a noble metal catalyst. Although any sources of oxygen and hydrogen are suitable, molecular oxygen and molecular hydrogen are preferred.

Thus, in a preferred embodiment of the invention, the epoxidation of propylene, hydrogen and oxygen is carried out in the presence of a titanium zeolite (in particular a titanium-MWW zeolite) and a noble metal.

The noble metal is preferably incorporated into the catalyst by supporting the noble metal on the titanium zeolite to form a noble metal-containing titanium zeolite, or alternatively, the noble metal may be first supported on a carrier such as an inorganic oxide, clay, carbon, or organic polymer resins, or the like, and then physically mixed with the titanium zeolite. There are no particular restrictions regarding the choice of noble metal compound used as the source of the noble metal. For example, suitable compounds include the nitrates, sulfates, halides (e.g., chlorides, bromides), carboxylates (e.g. acetate), and amine complexes of noble metals.

A preferred catalyst useful in the process of the invention is a noble metal-containing titanium zeolite, in particular a noble metal-containing titanium-MWW zeolite. Such catalysts typically comprise a noble metal (such as palladium, gold, platinum, silver, iridium, ruthenium, osmium, or combinations thereof) supported on a titanium zeolite. Noble metal-containing titanium zeolites are well known in the art and are described, for example, in JP 4-352771 and U.S. Pat. Nos. 5,859,265 and 6,555,493, the teachings of which are incorporated herein by reference in their entirety. The noble metal-containing titanium zeolites may contain a mixture of noble metals. Preferred noble metal-containing titanium zeolites comprise palladium and a titanium zeolite; palladium, gold, and a titanium zeolite; or palladium, platinum, and a titanium zeolite.

The typical amount of noble metal present in the noble metal-containing titanium zeolite will be in the range of from about 0.001 to 20 weight percent, preferably 0.005 to 10 weight percent, and particularly 0.01 to 5 weight percent.

Another preferred catalyst useful in the process of the invention is a catalyst mixture comprising a titanium zeolite (in particular a titanium-MWW zeolite) and a supported noble metal catalyst. The supported noble metal catalyst comprises a noble metal and a carrier. The carrier is preferably a porous material. Carriers are well-known in the art. For instance, the carrier can be inorganic oxides, clays, carbon, and organic polymer resins. Preferred inorganic oxides include oxides of Group 2, 3, 4, 5, 6, 13, or 14 elements. Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. The carrier may be a zeolite, but is not a titanium zeolite. Preferred organic polymer resins include polystyrene, styrene-divinylbenzene copolymers, crosslinked polyethyleneimines, and polybenzimidizole. Suitable carriers also include organic polymer resins grafted onto inorganic oxide carriers, such as polyethylenimine-silica. Preferred carriers also include carbon. Particularly preferred carriers include carbon, titania, zirconia, niobia, silica, alumina, silica-alumina, tantalum oxide, molybdenum oxide, tungsten oxide, titania-silica, zirconia-silica, niobia-silica, and mixtures thereof.

Preferably, the carrier has a surface area in the range of about 1 to about 700 $m^2/g$, most preferably from about 10 to about 500 $m^2/g$. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the carrier is in the range of about 0.1 μm to about 0.5 inch, more preferably from about 1 μm to about 0.25 inch, and most preferably from about 10 μm to about 1/16 inch. The preferred particle size is dependent upon the type of reactor that is used, for example, larger particle sizes are preferred for a fixed bed reaction. The average pore diameter is typically in the range of about 10 to about 1000 Å, preferably about 20 to about 500 Å, and most preferably about 50 to about 350 Å.

The supported noble metal catalyst also contains a noble metal. While any of the noble metals can be utilized (i.e., gold, silver, platinum, palladium, iridium, ruthenium, osmium), either alone or in combination, palladium, platinum, gold, a palladium/platinum, or a palladium/gold combination are particularly desirable. Palladium is most preferred.

Typically, the amount of noble metal present in the supported catalyst will be in the range of from 0.01 to 10 weight percent, preferably 0.01 to 4 weight percent. There are no particular restrictions regarding the choice of noble metal compound or complex used as the source of noble metal in the supported catalyst. For example, suitable compounds include the nitrates, sulfates, halides (e.g., chlorides, bromides), carboxylates (e.g. acetate), oxides, and amine complexes of the noble metal.

The catalyst useful in the process of the invention preferably contains lead, bismuth, or rhenium. The catalyst of the invention most preferably contains lead. As with the noble metal, lead, bismuth, or rhenium may be supported on the titanium zeolite or, alternatively, the lead, bismuth, or rhenium may be first supported on a carrier then physically mixed with the titanium zeolite.

Preferably, the catalyst will contain from about 0.001 to 5 weight percent of lead, bismuth, or rhenium and 0.01 to 10 weight percent of the noble metal. Most preferably, the catalyst contains 0.01 to 2 weight percent of lead, bismuth, and rhenium. Preferably, the weight ratio of noble metal to lead (bismuth or rhenium) in the catalyst is in the range of 0.1 to 10. While the choice of lead, bismuth, or rhenium compound used as the lead, bismuth, or rhenium source in the catalyst is not critical, suitable compounds include carboxylates (e.g., acetate, citrate), halides (e.g., chlorides, bromides, iodides), oxyhalides (e.g., oxychloride), carbonates, nitrates, phosphates, oxides, and sulfides. If used, the lead, bismuth, or rhenium may be added to the titanium zeolite or carrier before, during, or after noble metal addition.

Any suitable method may be used for the incorporation of the noble metal and optional lead, bismuth, or rhenium into the catalyst. For example, the noble metal and optional lead, bismuth, or rhenium may be supported on the titanium zeolite or the carrier by impregnation, ion-exchange, or incipient wetness techniques with, for example, palladium tetraammine chloride. If lead, bismuth, or rhenium is used, the order of addition of noble metal and optional lead, bismuth, or rhenium to the titanium zeolite or the carrier is not considered critical. However, it is preferred to add the lead, bismuth, or rhenium compound at the same time that the noble metal is introduced.

After noble metal and optional lead, bismuth, or rhenium incorporation, the noble metal-containing titanium zeolite or supported noble metal catalyst is recovered. Suitable catalyst recovery methods include filtration and washing, rotary evaporation and the like. The catalyst is typically dried prior to use in epoxidation. The drying temperature is preferably from about 50° C. to about 200° C. The catalyst may additionally comprise a binder or the like and may be molded, spray dried, shaped or extruded into any desired form prior to use in epoxidation.

After noble metal-containing titanium zeolite or supported noble metal catalyst formation, the catalyst may be optionally thermally treated in a gas such as nitrogen, helium, vacuum, hydrogen, oxygen, air, or the like. The thermal treatment temperature is typically from about 20° C. to about 800° C. It is preferred to thermally treat the catalyst in the presence of an oxygen-containing gas at a temperature from about 200° C. to 700° C., and optionally reduce the catalyst in the presence of a hydrogen-containing gas at a temperature from about 20° C. to 600° C.

In the epoxidation process of the invention, the catalyst may be used as a powder or as a large particle size solid. If a noble metal-containing titanium zeolite is used, the noble metal-containing zeolite may be used as a powder but is preferably spray dried, pelletized or extruded prior to use in epoxidation. If spray dried, pelletized or extruded, the noble metal-containing titanium zeolite may additionally comprise a binder or the like and may be molded, spray dried, shaped or extruded into any desired form prior to use in epoxidation. The noble metal-containing titanium zeolite may also be encapsulated in polymer as described in U.S. Pat. No. 7,030,255, the teachings of which are incorporated herein by reference in their entirety. If a catalyst mixture of titanium zeolite and supported noble metal catalyst is used, the titanium zeolite and supported catalyst may be pelletized or extruded together prior to use in epoxidation. If pelletized or extruded together, the catalyst mixture may additionally comprise a binder or the like and may be molded, spray dried, shaped or extruded into any desired form prior to use in epoxidation. The catalyst mixture may also be encapsulated in polymer as described in U.S. Pat. No. 7,030,255.

The epoxidation step of the process produces a product stream comprising propylene, propylene oxide, propylene glycol, tertiary butyl alcohol, and water. The product stream components are purified by a distillation process comprising three steps. The product stream may contain some residual hydrogen peroxide from the epoxidation reaction, however, if present, the residual hydrogen peroxide will decompose to water during the distillation steps. First, the product stream is distilled to produce a first overhead stream comprising propylene and a first bottoms stream comprising propylene oxide, propylene glycol, tertiary butyl alcohol, and water. In the first distillation, preferably at least 98% of the propylene (more preferably, at least 99.5%) is taken overhead.

If any hydrogen or oxygen is produced or left unreacted from the epoxidation step, the hydrogen or oxygen may be preferably removed by a flashing step prior to the first distillation. Alternatively, a vapor vent stream may be preferably removed from the first distillation to remove any hydrogen or oxygen that is produced or left unreacted from the epoxidation. The flashing or vapor vent stream may also include any inert gases used in the epoxidation step, such as nitrogen. The flashing or vapor vent stream will be especially useful in the case where epoxidation is performed using hydrogen and oxygen.

The first distillation is preferably conducted in a distillation tower wherein the top of the tower is preferably at 80-200 psig (0.65-1.48 MPa), and more preferably at 80-125 psig (0.55-0.86 MPa), and the bottom of the tower is preferably at 85-140 psig (0.58-0.96 MPa), and more preferably at 85-130 psig (0.58-0.89 MPa). The tower overhead temperature is preferably maintained between about −25 to 25° C., and more preferably at −20 to 15° C., and the bottoms temperature is preferably maintained between about 115-170° C., and more preferably between 125-140° C. The first distillation tower preferably has at least 10 theoretical stages, more preferably at least 20 stages, with a reflux ratio (lb reflux/lb distillate) preferably of at least 0.8, and more preferably between 0.8 to 4.0.

Preferably, the first overhead stream comprising propylene is recycled back to the epoxidation reactor. If a flashing or vapor vent stream comprising minor amounts of hydrogen and oxygen is taken, the vent stream may be recycled in part back to the reactor.

Following the first distillation, the first bottoms stream is distilled to produce a second overhead stream comprising propylene oxide and a second bottoms product stream comprising propylene glycol, tertiary butyl alcohol, and water. The second overhead stream comprising propylene oxide may be processed to further purify the propylene oxide if necessary.

The second distillation is preferably conducted in a distillation tower wherein the top of the tower is preferably at 40-70 psig (0.28-0.48 MPa), and more preferably at 50-60 psig (0.34-0.41 MPa) and the bottom is preferably at 50-80 psig (0.34-0.55 MPa), and more preferably 50-70 psig (0.34-0.48 MPa). The tower overhead temperature is preferably maintained between about 55-100° C., and more preferably between 65-85° C., and the bottoms temperature is preferably maintained between about 100-145° C., and more preferably between 110-130° C. The second distillation tower preferably has at least 10 theoretical stages, more preferably at least 20 stages, with a reflux ratio (lb reflux/lb distillate) preferably of at least 1, and more preferably between 1 to 20.

Following the second distillation, the second bottoms stream is distilled in a third distillation tower to produce a third overhead stream comprising an azeotrope of tertiary butyl alcohol and water and a third bottoms stream comprising propylene glycol and water.

Preferably, the azeotrope of tertiary butyl alcohol and water is recycled back to the epoxidation step for use a solvent.

The third distillation is preferably conducted in a distillation tower wherein the top of the tower is preferably at 10-50 psig (0.069-0.24 MPa), and more preferably at 15-30 psig (0.10-0.20 MPa) and the bottom is preferably at 15-60 psig (0.10-0.41 MPa), and more preferably 20-30 psig (0.13-0.21 MPa). The tower overhead temperature is preferably maintained between about 60-130° C., and more preferably between 70-90° C., and the bottoms temperature is preferably maintained between about 100-135° C., and more preferably between 105-125° C. The third distillation tower preferably has at least 10 theoretical stages, more preferably at least 20 stages, with a reflux ratio (lb reflux/lb distillate) preferably of at least 0.5, and more preferably between 0.7 to 1.5.

The third bottoms stream may be discarded as waste, but is preferably distilled to separate propylene glycol from the water. In an optional fourth distillation, a fourth overhead stream comprising water and a fourth bottoms stream comprising propylene glycol are produced.

The optional fourth distillation is preferably conducted in a distillation tower wherein the top of the tower is preferably at 0-30 psig (0-0.21 MPa), and more preferably at 5-20 psig (0.03-0.14 MPa) and the bottom is preferably at 5-35 psig (0.03-0.24 MPa), and more preferably 10-25 psig (0.07-0.17 MPa). The tower overhead temperature is preferably maintained between about 85-125° C., and more preferably between 95-115° C., and the bottoms temperature is preferably maintained between about 170-215° C., and more preferably between 180-205° C. The fourth distillation tower preferably has at least 5 theoretical stages, more preferably at least 10 stages, with a reflux ratio (lb reflux/lb distillate) preferably of at least 0.5, and more preferably between 0.7 to 1.1.

Overall, the process of the invention allows for the separation of a purified product stream of propylene oxide. The process of the invention also produces a stream containing a TBA-water azeotrope. The TBA and water of the azeotrope do not need to be separated before recycle back to the epoxidation step of the process.

The following examples merely illustrate the invention. Those skilled in the art will recognize many variations that are within the spirit of the invention and scope of the claims.

EXAMPLE 1

Three Tower Distillation Process

Propylene is continuously epoxidized over a Ti-MWW zeolite in the presence hydrogen peroxide in a solvent comprising TBA and water to produce an epoxidation product stream, comprising propylene, propylene oxide, propylene glycol, TBA, and water.

The epoxidation product stream is purified by a process as shown in FIG. 1. The epoxidation product stream is passed via line 1 to a first distillation tower 2. Tower 2 contains 15 ideal stages, 7 above feed and 8 below feed. The pressure is 120 psig (0.83 MPa) in the overhead and 125 psig (0.86 MPa) in the bottoms. The overhead temperature is 2.8° C. and the bottoms temp is 138° C. The reflux ratio is 3.0, by weight.

A first overhead stream is removed from the first distillation tower 2 via line 3. The first overhead stream contains the unreacted propylene. Stream 3 can be recycled back to the propylene epoxidation reactor.

The first bottoms stream from distillation tower 2 is removed via line 4. The first bottoms stream comprises propylene oxide, propylene glycol, TBA, and water. The first bottoms stream is passed via line 4 to second distillation tower 5.

Distillation tower 5 contains 40 ideal stages, 25 above feed and 15 below feed. The pressure is 55 psig (0.38 MPa) in the overhead and 60 psig (0.40 MPa) in the bottoms. The overhead temperature is 77° C. and the bottoms temp is 121° C. The reflux ratio is 10. The second overhead stream from distillation tower 5 is removed via line 6. The second overhead stream contains a purified propylene oxide stream.

The second bottoms stream is removed via line 7. The second bottoms stream comprises propylene glycol, TBA, and water. The second bottoms stream is passed via line 7 to third distillation tower 8.

Distillation tower 8 contains 20 ideal stages, 8 above feed and 12 below feed. The pressure is 20 psig (0.14 MPa) in the overhead and 25 psig (0.17 MPa) in the bottoms. The overhead temperature is 77° C. and the bottoms temp is 116° C. The reflux ratio is 1.1. The third overhead stream from distillation tower 8 is removed via line 9. The third overhead stream contains an azeotrope of TBA and water. The azeotrope of TBA and water can be recycled back to the propylene epoxidation reactor for use as a solvent mixture.

The third bottoms stream from distillation tower 8 is removed via line 10. The third bottoms stream comprises propylene glycol (PG) and water. The PG-water mixture can be sent to a waste stream or may be further distilled to separate PG from water.

If the PG-water mixture removed via line 10 is further distilled, the water column could contain 10 ideal stages, 5 above feed and 5 below feed. The pressure is 15 psig (0.1 MPa) in the overhead and 20 psig (0.14 MPa) in the bottoms. The overhead temperature is 101° C. and the bottoms temp is 198° C. The reflux ratio is 0.75.

The flow rates of the components of the various streams (in pounds per hour) are shown in Table 1.

This example shows that the use of a three distillation procedure effectively removes a purified propylene oxide stream (via line 6) and a TBA-water azeotrope stream (line 9) that can be recycled back to the propylene epoxidation reactor without further separation of TBA from water.

TABLE 1

| | Distillation Component Flow Rates (lb/h) | | | | | | |
|---|---|---|---|---|---|---|---|
| | Stream # | | | | | | |
| | 1 | 3 | 4 | 6 | 7 | 9 | 10 |
| Propylene | 55967 | 55967 | 0 | 0 | 0 | 0 | 0 |
| Propylene Oxide | 75000 | 0 | 75000 | 75000 | 0 | 0 | 0 |
| Propylene Glycol | 993 | 0 | 993 | 0 | 993 | 0 | 993 |
| TBA | 358866 | 0 | 358866 | 0 | 358866 | 358866 | 0 |
| Water | 117309 | 0 | 117309 | 0 | 117309 | 48937 | 68609 |
| Total | 608135 | 55967 | 552168 | 75000 | 477168 | 407803 | 69602 |

We claim:
1. A process for producing propylene oxide comprising:
(a.) contacting a titanium zeolite with a reaction feed comprising propylene, hydrogen peroxide, tertiary butyl alcohol, and water to produce a product stream comprising propylene, propylene oxide, propylene glycol, tertiary butyl alcohol, and water;
(b.) distilling the product stream to produce a first overhead stream comprising propylene and a first bottoms stream comprising propylene oxide, propylene glycol, tertiary butyl alcohol, and water;
(c.) distilling the first bottoms stream to produce a second overhead stream comprising propylene oxide and a second bottoms product stream comprising propylene glycol, tertiary butyl alcohol, and water; and distilling the second bottoms stream to produce a third overhead stream comprising an azeotrope of tertiary butyl alcohol and water and a third bottoms stream comprising propylene glycol and water.
2. The process of claim 1 wherein the titanium zeolite is a titanium-MWW zeolite.

3. The process of claim 1 wherein the hydrogen peroxide is formed by the in situ reaction of hydrogen and oxygen in the presence of a noble metal catalyst.

4. The process of claim 1, further comprising recycling the third overhead stream back to step (a).

5. The process of claim 1, further comprising distilling the third bottoms stream to produce a fourth overhead stream comprising water and a fourth bottoms stream comprising propylene glycol.

6. A process for producing propylene oxide comprising:
 (a) contacting a catalyst comprising a titanium-MWW zeolite and a noble metal with a reaction feed comprising propylene, hydrogen, oxygen, tertiary butyl alcohol, and water to produce a product stream comprising propylene, propylene oxide, propylene glycol, tertiary butyl alcohol, and water;
 (b) distilling the product stream to produce a first overhead stream comprising propylene and a first bottoms stream comprising propylene oxide, propylene glycol, tertiary butyl alcohol, and water;
 (c) distilling the first bottoms stream to produce a second overhead stream comprising propylene oxide and a second bottoms product stream comprising propylene glycol, tertiary butyl alcohol, and water; and
 (d) distilling the second bottoms stream to produce a third overhead stream comprising an azeotrope of tertiary butyl alcohol and water and a third bottoms stream comprising propylene glycol and water.

7. The process of claim 6 wherein the noble metal is palladium.

8. The process of claim 6 wherein the catalyst contains 0.01 to 10 weight percent of the noble metal and 0.001 to 5 weight percent of an additional metal selected from the group consisting of lead, bismuth, and rhenium.

9. The process of claim 6 wherein the catalyst comprises a noble metal supported on the titanium-MWW zeolite.

10. The process of claim 6 wherein the noble metal is supported on a carrier.

11. The process of claim 10 wherein the carrier is selected from the group consisting of carbon, titania, zirconia, niobia, silica, alumina, silica-alumina, tantalum oxide, molybdenum oxide, tungsten oxide, titania-silica, zirconia-silica, niobia-silica, and mixtures thereof.

12. The process of claim 6, further comprising recycling the third overhead stream back to step (a).

13. The process of claim 6, further comprising distilling the third bottoms stream to produce a fourth overhead stream comprising water and a fourth bottoms stream comprising propylene glycol.

\* \* \* \* \*